United States Patent [19]

Skuballa et al.

[11] Patent Number: 5,190,964
[45] Date of Patent: Mar. 2, 1993

[54] 5-FLUOROCARBACYCLINS, THEIR PREPARATION AND PHARMACEUTICAL USE

[75] Inventors: Werner Skuballa; Bernd Radüchel; Helmut Vorbrüggen; Martin Haberey; Claus-Steffen Stürzebecher; Michael-Harold Town, all of Berlin, Fed. Rep. of Germany

[73] Assignee: Schering Aktiengesellschaft, Berlin and Bergkamen, Fed. Rep. of Germany

[21] Appl. No.: 480,448

[22] Filed: Feb. 15, 1990

Related U.S. Application Data

[63] Continuation of Ser. No. 334,795, Apr. 3, 1978, abandoned, which is a continuation of Ser. No. 188,877, May 2, 1988, abandoned, which is a continuation of Ser. No. 77,278, Jul. 24, 1987, abandoned, which is a continuation of Ser. No. 804,225, Dec. 2, 1985, abandoned, which is a continuation of Ser. No. 539,218, Oct. 5, 1983, abandoned.

[30] Foreign Application Priority Data

Oct. 5, 1982 [DE] Fed. Rep. of Germany ....... 3237200

[51] Int. Cl.$^5$ ................ C07C 177/00; A61K 31/557
[52] U.S. Cl. ........................... 514/374; 514/530; 514/573; 514/623; 514/729; 548/237; 560/110; 560/119; 562/498; 562/501; 564/453; 568/819
[58] Field of Search ............... 560/119, 116; 548/237; 562/498, 501; 564/453; 568/819; 514/374, 530, 573, 623, 729

[56] References Cited

U.S. PATENT DOCUMENTS 4,306,076 12/1981 Nelson .......................... 514/277
4,497,830 2/1985 Skuballa ........................ 514/277

*Primary Examiner*—Robert Gerstl
*Attorney, Agent, or Firm*—Millen, White, Zelano and Branigan

[57] ABSTRACT 5-fluorocarbacyclin derivatives of the Formula I

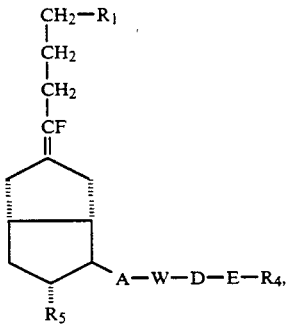

wherein
$R_1$ is $CH_2OH$ or
A is $-CH_2-CH_2-$, trans $-CH=CH-$ or $-C\equiv C-$,
W is a free or functionally modified hydroxymethylene group or free or functionally modified

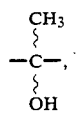

in which the OH group can be in the $\alpha-$ or $\beta$-position,
D is

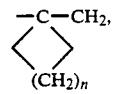

a $C_{1-10}$-aliphatic group (e.g., alkyl or alkenyl) which optionally can be substituted by fluorine atoms,
n is 1, 2 or 3,
E is a direct bond, $-C\equiv C-$ or $-CR_6=CR_7-$ in which $R_6$ represents a hydrogen atom or an alkyl group with 1-5 atoms and $R_7$ represents a hydrogen atom, a halogen atom or an alkyl group with 1-5 C atoms,
$R_4$ is alkyl, cycloalkyl or optionally substituted aryl or a heterocyclic group,
$R_5$ is a free or functionally modified hydroxy group and, when $R_2$ is a hydrogen atom, its salts with physiologically compatible bases,
have valuable pharmacological properties.

34 Claims, No Drawings

5-FLUOROCARBACYCLINS, THEIR PREPARATION AND PHARMACEUTICAL USE

This is a continuation of application Ser. No. 07/334,795 of Apr. 3, 1978 which a continuation of Ser. No. 07/188,877 of May 2, 1988, which is a cont. of Ser. No. 07/077,278 filed Jul. 24, 1987 which is a continuation of Ser. No. 804,225 of Dec. 2, 1985 which is a continuation of Ser. No. 06/539,218 of Oct. 5, 1983, (all are abandoned).

BACKGROUND OF THE INVENTION

This invention relates to new 5-fluorocarbacyclin derivatives, a process for preparing them and their use as pharmaceutical products.

German issued patents DE-OS 28 45 770; 29 00 352; 29 02 442; 29 04 655; 29 09 088; 30 48 906 and 29 12 409 described (5E) and (5Z) 6a-carbaprostaglandin-$I_2$ analogs. The nomenclature of the compounds according to this invention is based on a proposal of Morton and Brokaw (J. Org. Chem. 44 2280, 1979). In this synthesis including that described herein, two double-bond isomers, which are characterized by the notation (5E) or (5Z), always occur. Both isomers of the prototype are illustrated by the following structural formulae:

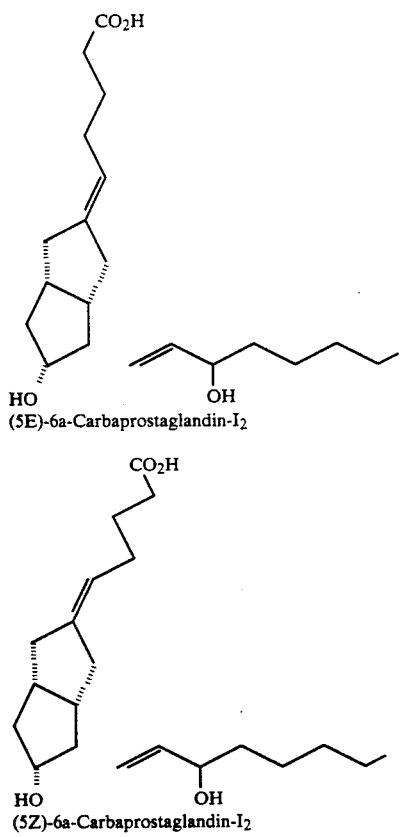

It is known from the extensive state of the art of prostacyclins and their analogs that this class of substances is suitable for treating mammals, including man, because of their biological and pharmacological properties. However, this use as pharmaceutical products often encounters difficulties, since they have a short duration of effect for therapeutic purposes. All structural changes are aimed at increasing the duration of effect and the selectivity of their effectiveness.

SUMMARY OF THE INVENTION

It is an object of this invention to provide new prostacyclin compounds having advantageous pharmacological properties.

Upon further study of the specification and appended claims, further objects and advantages of this invention will become apparent to those skilled in the art.

It has now been found that a longer duration of effect, a greater selectivity and a better effectiveness can be attained by substitution of the hydrogen atom in the 5-position of the carbacyclins with a fluorine atom. The resultant compounds of this invention are effective to lower blood pressure and as bronchial dilators inter alia. They are, moreover, suitable for vasodilation and inhibition of aggregation of blood platelets and of gastric acid secretion, inter alia.

The foregoing objects have been attained by providing 5-fluorocarbacyclin derivatives of formula I

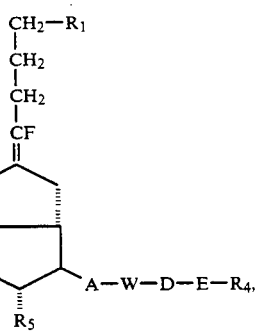

wherein
$R_1$ is $CH_2OH$ or

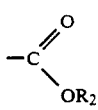

wherein $R_2$ is hydrogen, alkyl, cycloalkyl, aryl, a

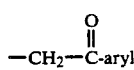

or a heterocyclic radical, or
$R_1$ is

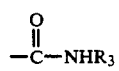

wherein $R_3$ is alkanoyl or an alkane sulfonyl radical each of 1-10 C atoms or a group $R_2$ as defined above, or
$R_1$ is

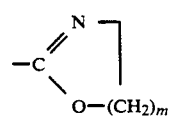

wherein m is the number 1 or 2,

A is —CH$_2$—CH$_2$—, trans—CH=CH— or —C≡C—

W is a free or functionally modified hydroxymethylene group or a free or functionally modified

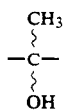

group, in which the OH group can be in α- or β-position,

D is

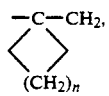

a straight-chain saturated alphatic group of 1-10, e.g., 1-5 carbon atoms, a branched, saturated or a straight-chain or branched unsaturated alphatic group of 2-10, e.g., 2-5 C-atoms, all of which optionally can be substituted by fluorine atoms, n is 1, 2 or 3, E is a direct bond, —C≡C— or —CR$_6$=CH$_7$— in which R$_6$ represents a hydrogen atom or an alkyl group with 1-5 atoms and R$_7$ represents a hydrogen atom, a halogen atom or an alkyl group with 1-5 C atoms, R$_4$ is alkyl, cycloalkyl, an optionally substituted aryl group or a heterocyclic group, and R$_5$ is a free or functionally modified hydroxy group, and, when R$_2$ is hydrogen, the salts thereof with physiologically compatible bases.

DETAILED DISCUSSION

The compounds of Formula I include (5E)- as well as (5Z)-isomers.

Suitable alkyl groups R$_2$ include straight or branched-chain alkyl groups of 1-10 carbon atoms, e.g., methyl, ethyl, propyl, isopropyl, butyl, isobutyl, tert-butyl, pentyl, isopentyl, neopentyl, heptyl, hexyl, decyl, etc. The alkyl groups R$_2$ can optionally be mono- to polysubstituted (e.g., 2-5 substituents) by halogen atoms, hydroxy groups, C$_1$-C$_4$-alkoxy groups, optionally substituted C$_6$-C$_{10}$-aryl groups, di-C$_1$-C$_4$-alkylamino, and tri-C$_1$-C$_4$-alkylammonium. Suitable substituted aryl groups include those described below for R$_2$ per se. Mono-substituted alkyl groups are preferred. Examples of substituents include fluorine, chlorine, bromine, phenyl, dimethylamino, diethylamino, methoxy, ethoxy, etc. Preferred alkyl groups R$_2$ are those of 1-4 carbon atoms in the alkyl portion, e.g., methyl, ethyl, propyl, dimethylaminopropyl, isobutyl, butyl, etc.

Suitable aryl groups R$_2$ include substituted as well as unsubstituted aryl groups, for example phenyl, 1-naphthyl, and 2-naphthyl, each of which can be substituted by 1-3 halogen atoms, phenyl, 1-3 alkyl groups each of 1-4 carbon atoms, or a chloromethyl, fluoromethyl, trifluoromethyl, carboxy, hydroxy, or alkoxy group of 1-4 carbon atoms. Preferred is substitution in the 3- and 4-positions on the phenyl ring, for example by fluorine, chlorine, alkoxy, or trifluoromethyl, or in the 4-position by hydroxy.

Suitable cycloalkyl groups R$_2$ contain 3-10, preferably 5 or 6 carbon atoms in the ring. The rings can be substituted by alkyl groups of 1-4 carbon atoms. Examples include cyclopentyl, cyclohexyl, methylcyclohexyl, and adamantyl.

Suitable heterocyclic groups R$_2$ include 5- and 6-membered heterocycles containing at least one hetero atom, preferably nitrogen, oxygen, or sulfur, usually on such atom. The rings are normally aromatic. Examples include 2-furyl, 3-furyl, 2-thienyl, 3-thienyl, 2-pyridyl, 3-pyridyl, 4-pyridyl and others.

The aryl group in the

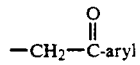

group for R$_2$ can be phenyl, α- or β-naphthyl, and each can be substituted by (a) 1-3 phenyl groups, which latter, in turn, can be substituted by 1-3 halogen atoms, such as F, Cl, or Br; or by (b) 1-3 C$_1$-C$_4$-alkoxy groups or by (c) 1-3 halogen atoms (f, Cl, Br). Single substitution by phenyl, C$_1$-C$_2$-alkoxy, chlorine, or bromine is preferred.

Suitable acid residues R$_3$, i.e., acyl groups, include physiologically compatible acid residues. Preferred acids are organic carboxylic acids and sulfonic acids of 1-10 carbon atoms pertaining to the aliphatic, cycloaliphatic, aromatic, aromatic-aliphatic, and heterocyclic series. These acids can be saturated, unsaturated and/or polybasic and/or substituted in the usual way. Examples of substituents are C$_1$-C$_4$-alkyl, hydroxy, C$_1$-C$_4$-alkoxy, oxo, or amino groups, or halogen atoms (F, Cl, Br). Thus while the acids are often hydrocarbon in nature, many diverse equivalents exist and will be readily recognized by those of skill in the art.

The following carboxylic acids are recited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecyclic acid, myristic acid, pentadecyclic acid, trimethylacetic acid, cyclopropanecarboxylic acid, cyclohexanecarboxylic acid, phenylacetic acid, phenoxyacetic acid, methoxyacetic acid, ethoxyacetic acid, mono-, and di-, and trichloroacetic acids, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy, or carboxy groups, nicotinic acid, isonicotinic acid, furan-2-carboxylic acid, cyclopentylpropionic acid, etc. Especially preferred acyl residues are those of up to 10 carbon atoms. Examples of suitable sulfonic acids include methanesulfonic acid, ethanesulfonic acid, isopropanesulfonic acid, β-chloroethanesulfonic acid, butanesulfonic acid, benezenesulfonic acid, p-toluenesulfonic acid, p-chlorobenzenesulfonic acid, N,N-dimethylaminosulfonic acid, N,N-diethylaminosulfonic acid, N-N-bis(β-chloroethyl)aminosulfonic acid, N,N-diisobutylaminosulfonic acid, N,N-dibutylaminosulfonic acid pyrrolidino-, piperidino-, piperazin-, N-methylpiperazino-, and morpholinosulfonic acids.

The hydroxy groups R$_5$ and those in W can be functionally modified, for example by etherification or esterification, wherein the free or modified hydroxy groups in W can be in the α- or β-position, free hydroxy groups being preferred.

The many suitable ether and acyl residues are well known to persons skilled in the art. Ether residues that can be easily split off are preferred, e.g., tetrahydropyranyl, tetrahydrofuranyl, α-ethoxyethyl, trimethylsilyl, dimethyl-tert-butylsilyl, and tribenzylsilyl. Suitable acryl residues include those mentioned for $R_3$. Thus, generally, these are $C_{1-10}$-hydrocarbon carboxylic and sulfonic acids and equivalents. Worth mentioning by name, for example, are acetyl, propionyl, butyryl, benzoyl, etc.

Suitable alphatic groups $R_4$ include straight chained and branched, saturated (alkyl) and unsaturated (e.g., alkenyl) aliphatic residues, preferably alkyl groups, of 1–10, especially 1–7 carbon atoms which can optionally be substituted by optionally substituted aryl. Suitable substituents, on the latter aryl substituents, are those mentioned for the $R_2$ aryl groups per se. Examples include methyl, ethyl, propyl, butyl, isobutyl, tert-butyl, pentyl, hexyl, heptyl, octyl, butenyl, isobutenyl, propenyl, pentenyl, hexenyl, benzyl, and p-chlorobenzyl.

Cycloalkyl groups $R_4$ can contain 3–10, preferably 3–6 carbon atoms in the ring. The rings can also be substituted by alkyl groups of 1–4 carbon atoms. Examples include cyclopropyl, cyclobutyl, cyclopentyl, cyclohexyl, methylcyclohexyl, and adamantyl.

Examples of substituted and unsubstituted aryl groups $R_4$, includes: phenyl, 1-naphthyl and 2-naphthyl, each of which can be substituted by 1–3 halogen atoms, phenyl, 1–3 alkyl groups of 1–4 carbon atoms each, or a chloromethyl, fluoromethyl, trifluoromethyl, carboxy, $C_1$–$C_4$-alkoxy, or hydroxy group. Substitution in the 3- and 4-positions on the phenyl ring is preferred, for example by fluorine, chlorine, $C_1$–$C_4$-alkoxy, or trifluoromethyl, or in the 4-position by hydroxy.

Suitable heterocyclic groups $R_4$ includes 5- and 6-membered heterocycles containing at least one hetero atom, preferably nitrogen, oxygen, or sulfur, usually one such atom. The rings are usually aromatic. Examples include 2-furyl, 2-thienyl, 2-pyridyl, 3-pyridyl, 4-pyridyl, 3-furyl, 3-thienyl, etc.

The aliphatic groups D can be straight-chained or branched, saturated (alkylene) or unsaturated (alkenylene) residues, preferably saturated ones (alkylene) of 1–10, especially 1–5 carbon atoms which can optionally be substituted by fluorine atoms. Examples include: methylene, fluoromethylene, ethylene, 1,2-propylene, ethylethylene, trimethylene, tetramethylene, pentamethylene, 1-methyltetramethylene, 1-methyltrimethylene, etc., or also 1,1-alkylene-ethylene

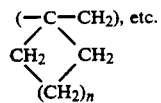

The alkyl groups $R_6$ and $R_7$ can be straight-chained or branched, alkyl groups of 1–5 carbon atoms, as mentioned above for $R_2$ and $R_4$. Suitable $R_6$ and $R_7$ halogen atoms include chlorine and bromine, preferably chlorine.

The many conventional inorganic and organic bases suitable for salt formation with the free acids ($R_2$=H), are known to those skilled in the art for the formation of physiologically compatible salts with prostaglandin-type compounds. Examples include: alkali metal hydroxides, such as sodium and potassium hydroxide, alkaline earth metal hydroxides, such as calcium hydroxide, ammonia, amines, such as ethanolamine, diethanolamine, triethanolamine, N-methylglucamine, morpholine, tris(hydroxymethyl) methylamine, etc.

This invention further relates to a process for producing the 5-fluorocarbacyclin derivatives of this invention, comprising in fully conventional manner, reacting a compound of formula II,

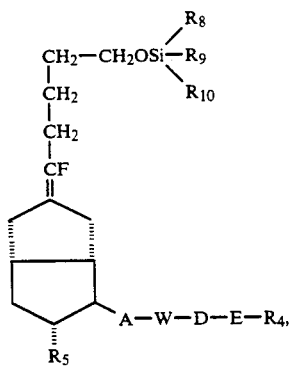

wherein $R_4$, $R_5$, A, W, D and E are as defined above and $R_8$, $R_9$ and $R_{10}$ can be the same or different and are a straight-chained or branched alkyl group of 1–10 carbon atoms or an aryl group, possibly after conventional protection of the free hydroxy groups which are present, with a conventional reagent which is suitable for splitting the silyl groups, and optionally, in any sequence, then separating isomers, and/or releasing protected hydroxy groups, and oxidizing the 1-hydroxy group to form the 1-carboxyl group ($R_1$=COOH), and/or releasing protected hydroxy groups, and/or esterifying or etherifying free hydroxy groups, and/or esterifying a free carboxyl group, and/or saponifying an esterified carboxyl group or converting a carboxyl group into an amide or $\Delta^2$-oxazoline or a salt with a physiologically compatible base.

splitting off of the silylether groups in the compounds of formula II can be effected with a tetraalkylammonium fluoride, preferably, tetrabutylammonium fluoride, or an alkali or alkaline earth metal fluoride in an inert solvent, for example, tetrahydrofuran, diethyl ether, dioxane, dimethyloxyethane, methylene chloride, dimethylflormamide, dimethyl sulfoxide, etc., at temperatures of 0° C. to 80° C., preferably, 20° C. to 45° C.

Oxidation of a 1-hydroxy group is performed by methods known to those skilled in the art. There can be used as oxidation agents, for example: pyridinium dichromate (Tetrahedron Letters, 1979, 399), Jones reagent (J. Chem. Soc. 1953, 2555) or platinum/oxygen (Adv. in Carbohydrate Chem., 17, 169, 1962); or Collins oxidation and then Jones oxidation can be performed. The oxidation with pyridinium dichlormate is performed at temperatures from 0° C. to 100° C., preferably 20° C. to 40° C. in a solvent that is inert to the oxidation agent, for example, dimethylformamide. Oxidation with Jones reagent is performed at temperatures from −40° C. to +40° C., preferably 0° C. to 30° C. in acetone as the solvent. Oxidation with platinum/oxygen is performed at temperatures from 0° C. to 60° C., preferably 20° C. to 40° C. in a solvent that is inert to the oxidation agent, for example, acetic ester.

Saponification of the carbacyclin esters is performed by methods known to those skileld in the art, for example, with basic catalysts.

Introduction of the ester group

for $R_1$, in which $R_2$ is an alkyl group of 1-10 C atoms, or cycloalkyl, occurs according to methods known to those skilled in the art. The carboxy compounds can be reacted, for example, with diazohydrocarbons in a way known in the art. Esterifications with diazohydrocarbons can be effected, for example, as follows. A solution of diazohydrocarbons is mixed in an inert solvent, preferably in diethyl ether with the carboxy compound in the same or another inert solvent, for example, methylene chloride. After the reaction is completed in 1 to 30 minutes, the solvent is removed and the ester is purified in the usual way. Diazoalkanes are either known or can be produced by known methods (Org. Reactions, Vol. 8, pages 389-394, 1954).

Introduction of the ester group

for $R_1$, in which $R_2$ represents a substituted or unsubstituted aryl group or hetero group, also occurs according to methods known to a man skilled in the art. For example, the carboxy compounds and the corresponding aryl or other hydroxy compounds can be reacted with dicyclohexylcarbodiimide in the presence of a suitable base, for example, pyridine or triethylamine in an inert solvent. Possible solvents include methylene chloride, ethylene chloride, chloroform, acetic ester, tetrahydrofuran, preferably, chloroform. The reaction is performed at temperatures of $-30°$ C. to $+50°$ C., preferably at $+10°$ C.

Introduction of the ester group

for $R_1$ can also be accomplished by conventional reaction of the carboxylate anion with the corresponding alkyl halide or $\omega$-halogen ketone

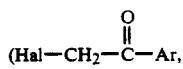

in which Ar is phenyl, or diphenyl, which can be substituted by $C_1$-$C_2$ alkoxy or chlorine or bromine etc.).

The introduction of the $\Delta^2$-oxazoline group

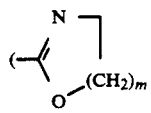

for $R_1$ can be done according to the processes described in DE-OS 30 47 759; 31 15 997 and 31 45 830 whose disclosures are incorporated by reference herein as are all of those mentioned herein. For example, the carboxy compounds converted into the $\Delta$-$^2$oxazolinesnes in the presence of the corresponding amino alcohols with tert-phosphines, especially triphenyl phosphin in the presence of halogen compounds especially carbon tetrachloride and tertiary base, preferably triethylamine or DBN.

The carbacyclin derivatives of formula I wherein $R_2$ is a hydrogen atom can be converted into salts with suitable amounts of the corresponding inorganic bases during conventional neutralization reactions. For example, the solid inorganic salt can be obtained by dissolving the corresponding acids in water which contains a stoichiometric amount of the base, after evaporation of the water or after addition of a solvent miscible with water, for example, alcohol or acetone.

Production of the amine salts also occurs in the usual way. For this purpose, carbacyclin acid, for example, is dissolved in a suitable solvent, such as ethanol, acetone, diethyl ether or benzene, and at least a stoichiometric amount of the amine is added to this solution. In this way, the salt, usually in solid form, is precipitated or isolated in the usual way after evaporation of the solvent.

Functional modification of the free OH group occurs by the methods known to a man of the art. For example, for introduction of the ether protective groups reaction can be performed with dihydropyran in methylene chloride or chloroform using an acid condensation agent, for example, p-toluene sulfonic acid. The dihydropyran is used in excess, for example, in 4 to 10 times the amount required by theory. The conversion normally at $0°$ to $30°$ C. ends after 15 to 30 minutes.

Introduction of the acyl protective groups can be accomplished by reacting a compound of formula I, in a way known in the art, with a carboxylic acid derivative, for example, an acid chloride, acid anhydride, among others.

Release of a functionally modified OH group to form the corresponding compounds of formula I occurs by known methods. For example, splitting off of the ether protective groups is performed in an aqueous solution of an organic acid, for example, acetic acid, propionic acid, among others, or in an aqueous solution of an inorganic acid, for example, hydrochloric acid. It is advantageous to add a water-miscible inorganic solvent to the compound to improve solubility. Suitable organic solvents include, for example, alcohols, such as methanol and ethanol, and ethers, such as dimethoxyethane, dioxane and tetrahydrofuran. Tetrahydrofuran is preferably used. Splitting off preferably is performed at temperatures of $20°$ C. to $80°$ C.

Splitting off of the silyl ether protective groups occurs, for example, with tetrabutylammonium fluoride. Solvents include, for example, tetrahydrofuran, diethyl ether, dioxane, methylene chloride, etc. The splitting off is preferably performed at temperatures of $0°$ C. to $80°$ C.

Saponification of the acyl groups occurs, for example, with alkali or alkaline earth metal carbonates or hydroxides in an alcohol or aqueous alcohol solution. Suitable alcohols include aliphatic alcohols, for example, methanol, ethanol, butanol, etc., preferably methanol. Potassium and sodium salts, but preferably potassium salts, can be cited as alkali metal carbonates and hydroxides. Calcium carbonate, calcium hydroxide and barium carbonate, for example, are suitable as alkaline earth metal carbonates and hydroxides. The reaction occurs at $-10°$ C. to $70°$ C., preferably at $25°$ C.

Introduction of the amide group

for $R_1$ also occurs by methods known to those skilled in the art. For example, carboxylic acids of formula I ($R_2=H$) are converted into a mixed anhydride in the presence of a tertiary amine, for example, triethylamine, with chloroformic acid isobutyl ester. Reaction of the mixed anhydride with the alkali metal salt of the corresponding amide or with ammonia ($R_3=H$) occurs in an inert solvent or solvent mixture, for example, tetrahydrofuran, dimethoxyethane, dimethylformamide, hexamethylphosphonic acid amide etc. at temperatures of $-30°$ C. to $+60°$ C., preferably at $0°$ C. to $30°$ C.

Another possibility for introduction of the amide group

for $R_1$ involves the reaction of a 1-carboxylic acid of formula I ($R_2=H$), possibly intermediately protected in its free hydroxy groups, with the compounds of formula III, $$O\!=\!C\!=\!N\!-\!R_3 \qquad\qquad III$$

wherein $R_3$ is as defined above.

Reaction of a compound of formula I ($R_2=H$) with an isocyanate of formula IV occurs possibly with addition of a tertiary amine, for example, triethylamine or pyridine. The reaction can be performed without solvent or in an inert solvent, preferably acetonitrile, tetrahydrofuran, acetone, dimethyl acetamide, methylene chloride, diethyl ether, toluene, at temperatures of $-80°$ C. to $100°$ C., preferably at $0°$ C. to $30°$ C.

If the starting material contains OH groups in the prostane radical, these OH groups are used for the reaction. If end products containing free hydroxyl groups in the prostane radical are desired, starting materials are advantageously used in which they preferably are intermediarily protected by ether or acyl radicals that are easy to split off.

Compounds of formula II serving as starting materials herein can, for example, be produced in a way well known in the art, by reacting an aldehyde of formula IV (DE-OS 28 45 770)

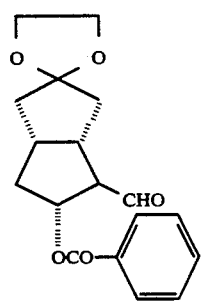

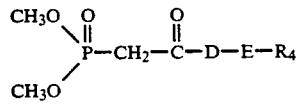

wherein D, E and $R_4$ are as defined above, in the presence of a deprotonizing agent, such as a sodium hydride or potassium tert-butylate, to form a ketone of formula VI ($X=H$) or additionally in the presence of a brominating agent such as N-bromosuccinimide to form a ketone of formula VI ($X=Br$).

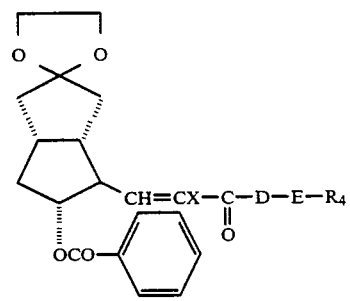

After reduction of the keto group with zinc borohydride or sodium borohydride or reaction with alkyl magnesium bromide or alkyl lithium and then epimer separation, the compounds of formula VII are obtained

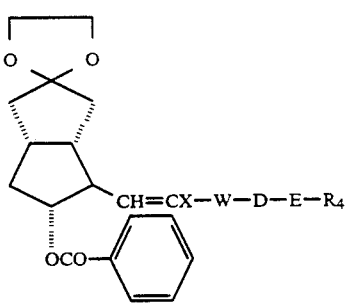

Conventional saponification of the ester group, for example with potassium carbonate in methanol, as well as optional hydrogenation of the double bond or optional etherification with dihydropyran and the elimination of the hydrogen bromide, for example, with potassium tert-butylate in dimethyl sulfoxide, ketal cleavage with aqueous acetic acid as well as optional functional modification of the free hydroxy groups, for example, by etherification with dihydropyran and subsequent splitting off, yields the ketone of formula VIII.

The conventional reaction of ketone VIII with a carbanion produced for the ester of formula IX $$R_{11}OOC\!-\!CHF\!-\!CH_2CH_2CH_2CH_2OSi\!\genfrac{}{}{0pt}{}{\diagup R_8}{\diagdown R_{10}}\!R_9 \qquad IX$$

wherein $R_8$, $R_9$, $R_{10}$ are as defined above and $R_{11}$ is an alkyl group of 1-5 carbon atoms, and lithium diisopropylamide yields, after saponification, for example, with alcoholic potassium hydroxide, the corresponding acid of formula X.

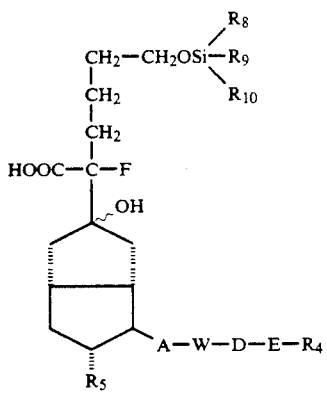

The conventional dehydration decarboxylation of the hydrocarboxylic acid of formula X with dimethylformamide acetate or arylsulfonic acid chloride and pyridine and then heat treatment of the intermediate β-lactone yields the 5-fluorolefin of formula II.

Production of the phosphonate of formula V occurs in a way known in the art by reaction of the anion of methylphosphonic acid dimethyl ester with an ester of formula XI

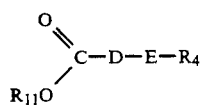

wherein D, E, $R_4$ are as defined above and $R_{11}$ is an alkyl group of 1-5 C atoms, which is possibly obtained from the corresponding malonic acid ester by alkylation with the halide of formula XII

with Hal being chlorine or bromine, and subsequent decarboxylation. The ester of formula XI also can be obtained from the carboxylic acid of formula XIII

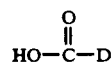

wherein D is as defined above by alkylation with the halide of formula XII and subsequent esterification.

Production of the fluoro esters of formula IX occurs in a way known in the art by selective silylation of 1,4-butanediol and subsequent oxidation, for example, with Collins reagent or pyridinium dichromate to aldehyde XIV

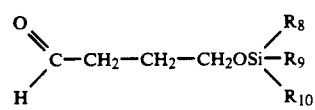

After olefinizing reaction with phosphonic fluoracetic acid triethyl ester and subsequent catalytic hydrogenation, the ester of formula IX is obtained.

The compounds of this invention have blood-pressure-lowering and bronchodilatory effects. They are furthermore suitable for inhibiting thrombocyte aggregation. Consequently, the novel carbacyclin derivatives of Formula I represent valuable pharmacologically active agents. Moreover, with a similar spectrum of activity, they exhibit a higher specificity as compared with corresponding prostaglandins and, above all, a substantially longer efficacy. As compared with $PGI_2$, they are distinguished by higher stability.

The high tissue specificity of the novel prostaglandins is demonstrated in a study on smooth-muscle organs, such as, for example, on the guinea pig ileum or on the isolated rabbit trachea, where a substantially lower stimulation can be observed than in the administration of natural prostaglandins of the E-, A-, or F-type.

The novel carbacyclin analogs also exhibit the properties typical for prostacyclins, such as, for example, lowering of peripheral arterial and coronary vascular resistance, inhibition of thrombocyte aggregation and dissolution of platelet thrombi, myocardial cyto-protection and thus lowering of systemic blood pressure without simultaneously lowering stroke volume and coronary blood flow; treatment for stroke, prophylaxis and therapy of coronary heart disease, coronary thrombosis, cardiac infraction, peripheral arterial diseases, arteriosclerosis and thrombosis, prophylaxis and therapy of ischemic attacks of the CNS system, therapy for shock, inhibition of bronchoconstriction, inhibition of gastric acid secretion, cytoprotection for gastric and intestinal mucosa, cytoprotection in liver and pancreas, antiallergic properties, lowering of pulmonary vascular resistance and pulmonary blood pressure, promotion of kidney blood flow. utilization in place of heparin or as an adjuvant in dialysis of hemofiltration, preservation of blood plasma stores, especially blood platelet stores, inhibition of labor, treatment of gestational toxicosis, enhancement of cerebral blood flow, etc. In addition, the novel carbacyclin derivatives exhibit antiproliferative and antidiarrheogenic properties. The carbacyclins of this invention can also be utilized in combination, for example with β-blockers, diuretics or phosphodiesterase inhibitors.

The novel prostaglandin analogs of this invention are substantially more selective with regard to potency, as compared with known PG analogs, in causing prostaglandin-like biological responses, and have a substantially longer duration of biological activity. Accordingly, each of these novel prostaglandin analogs is surprisingly and unexpectedly more useful than one of the corresponding conventional prostaglandin-type compounds for at least one of the pharmacological purposes indicated above, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

The usual dosage of the compounds is 1-1,500 µg/kg/day when administered to human patients. The unit dosage for the pharmaceutically acceptable carrier is usually 0.01-100 mg. Precise dosages in a given case can be readily determined using fully conventional methods, e.g., by differential potency tests vis a vis a known analogous agent such as $PGI_2$. In general, the administration of the compounds of this invention will be analogous to that of a related known agent, e.g., PGI$_2$.

Upon intravenous injection administered to nonanesthetized, hypertonic rats in doses of 5, 20, and 100 µg/kg of body weight, the compounds of this invention exhibit a stronger blood-pressure-lowering effect and a more prolonged duration of efficacy than PGE$_2$ and PGA$_2$ without triggering diarrhea, as does PGE$_2$, or cardiac arrhythmias, as does PGA$_2$.

Upon intravenous injection administered to narcotized rabbits, the compounds of this invention show, as compared with PGE$_2$ and PGA$_2$, a stronger and also considerably prolonged blood-pressure-lowering effect without affecting other smooth-muscle organs or organ functions.

Sterile, injectable, aqueous or oily solutions are used for parenteral administration. Suitable for oral administration are, for example, tablets, dragees, or capsules. The invention accordingly also concerns medicinal agents based on the compounds of Formula I and conventional auxiliary agents and excipients. Thus, the active agents of this invention can serve, in conjunction with the excipients known and customary in galenic pharmacy, for example for the preparation of blood-pressure-lowering agents or agents corresponding to the many other uses of this invention.

The pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene gylcols, gelatine, lactose, amylose, magnesium stearate, talc, silicic acid, viscous paraffin, perfume oil, fatty acid monoglycerides and diglycerides, pentaerythritol fatty acid esters, hydroxy-methyl-cellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in anyway whatsoever. In the following example(s) all temperatures are set forth uncorrected in degrees Celsius; unless otherwise indicated, all parts and percentages are by weight.

EXAMPLE 1

(5Z)-(16RS)-5-fluoro-16-methyl-18,18,19,19-tetradehydro-6a-carba-prostaglandin-I$_2$ 0.93 g of tetrabutylammonium fluoride is added to a solution of 960 mg of (5E,2)-(16RS-2-decarboxy-5-fluoro-16-methyl-2-(dimethyl-tert-butyl-silyloxymethyl)-18,18,19,19-tetradehydro-6a-carba-prostaglandin I$_2$-11,15-bis-(tetrahydropyranyl ether) in 30 ml of tetrahydrofuran and stirred for 6 hours at 25° C. Then, it is diluted with ether, agitated three times with water, dried in magnesium sulfate and evaporated under vacuum. The residue is chromatographed with hexane/ether (3+2) on silica gel. Thus there are obtained as the more polar component 360 mg of (5E)-(16RS)-2-decarboxy-5-fluoro-2-hydroxymethyl-16-methyl-18,18,19,19-tetradehydro-6a-carba-prostaglandin-I$_2$-11,15-bis-(tetrahydropyranyl ether) and as the more nonpolar component 380 mg of (5Z)-(16RS)-2-decarboxy-5-fluoro-2-hydroxymethyl-16-methyl-18,18,19,19-tetradehydro-6a-carba-prostaglandin-I$_2$-11,15-bis-(tetrahydropyranyl ether).

IR (CHCl$_3$): 3650, 2930, 2865. 1600, 972/cm

For oxidation of the 1-hydroxy group, 380 mg of 5% configured fluorolefin are dissolved in 10 ml of methylene chloride, mixed at 0° C. with 1.8 g of Collins reagent (chromic acid-pyridine complex) and stirred for 15 minutes at 0° C. Then it is mixed with a mixture of ether/hexane (3+2), filtered, the filtrate is successively washed with water, 10% sulfuric acid and water, dried on magnesium sulfate and evaporated under vacuum. Then the resulting aldehyde is dissolved in 16 ml of acetone and mixed drop by drop with 1.6 ml of Jones reagent at −20°C. It is stirred for 30 minutes at −20° C., 2 ml of isopropyl alcohol are added, diluted with ether, agitated three times with water, dried on magnesium sulfate and evaporated under vacuum.

For splitting off of the protection group, the evaporation residue is stirred for 16 hours at 25° C. with 30 ml of acetic acid/water/tetrahydrofuran (65/35/10). It is evaporated with addition of toluene and the residue is chromatographed on silica gel with acetic ester/0.1-1% acetic acid, and 245 mg of the compound of the title are obtained as a colorless oil.

IR: 3600, 3400 (broad), 2920, 2870, 1719, 1602, 1430, 969/cm.

The starting material for the compound of the above title is produced as follows:

1a)
(5E,Z)-(16RS)-2-decarboxy-5-fluoro-16-methyl-2-(dimethyl-tert-butylsilyloxymethyl)-18,18,19,19-tetradehydro-6a-carba-prostaglandin-I$_2$-11,15-bis-(tetrahydropyranyl ether).

A solution of 2.8 ml of diisopropylamine in 10 ml of tetrahydrofuran is mixed at −25° C. within 15 minutes with 12.3 ml of a 1.62 molar solution of butyllithium in hexane and stirred for 1 hour at −25° C. A solution of 5.8 a of 2-fluoro-6-(dimethyl-tert-butylsilyloxy)-caproic acid ethyl ester in 5 ml of tetrahydrofuran is dripped into the mixture at −70° C. within 10 minutes. It is stirred for 10 minutes at −70° C. solution of 2.2 g of (1R,5S,6R,7R)-7-(tetrahydrofuran-2-yloxy)-6-[(E)-(3S-4RS)-4-methyl-3-(tetrahydropyran-2-yloxy)-oct-1-ene- 6-inyl]-bicyclo[3.3.0]octan-3-one in 15 ml of diethyl ether and 15 ml of tetrahydrofuran are added, stirred for 1 hour at −70° C., mixed with 100 ml of saturated ammonium chloride solution and acidified with 10% citric acid to pH5. It is extracted with ether, the organic phase is washed with water until neutral, dried on magnesium sulfate and evaporated under vacuum. After chromatography on silica gel, 1.8 g of α-fluoro ester are obtained with hexane/ether, stirred at 25° C. for 7 hours for saponification with 25 ml of an ethanol potassium hydroxy solution (production: 5 g of potassium hydroxide is dissolved in 187 ml of ethanol and 62 ml of water). It is acidified to pH4 with 10% citric acid solution, extracted with methylene chloride, the organic extract is washed with water until neutral and dried on magnesium sulfate.

The evaporation residue is dissolved in 35 ml of pyridine, 880 mg of benzenesulfonic acid chloride are added at 0° C. and stirred for 24 hours at 0° C. It is then mixed with 1.5 ml of water, stirred for 1 hour, diluted with ether, agitated with saturated sodium bicarbonate solution, washed three times with water, dried on magnesium sulfate and evaporated under vacuum. The residue is stirred for 3 hours at 100° C. in 20 ml of pyridine and evaporated with addition of toluene under vacuum. The residue is chromatographed with hexane/ether (9+1) on silica gel. Thus, 1.1 g of the compound of the title is obtained as a colorless oil.

IR: 2945, 2868, 1450, 971, 862, 835/cm.

1b) Production of 2-fluoro-6-(dimethyl-tert-butylsilyloxy)-caproic acid ethyl ester 51 g of imidazole and 45 g of dimethyl-tert-butylsilyl chloride are added to a solution of 27 g of 1,4-butanediol in 50 ml of dimethylformamide at 0° C. and stirred for 24 hours at 0° C. Then it is poured on 400 ml of water, extracted with a mixture of ether/pentane (1+1), the organic phase is successively washed with 5% sulfuric acid, 5% sodium bicarbonate solution and water. It is dried on magnesium sulfate and evaporated under vacuum. After filtration on silica gel with hexane/ether (1+1), 18 g of 1-(dimethyl-tert-butylsilyloxy)-butan-4-ol are obtained as a colorless liquid.

90 g of Collins reagent are added to a solution of 12 g of the monosilyl ether produced above in 600 ml of methylene chloride at 0° and stirred for 30 minutes at 0° C. It is then diluted with ether and agitated successively with 5% sodium bicarbonate solution, water, 10% citric acid solution, 5% sodium bicarbonate solution and water. It is dried on magnesium sulfate and evaporated under vacuum.

24 g of phosphonofluoroacetic acid ethyl ester in 60 ml of dimethoxyethane are dripped into a suspension of 3.9 g of sodium hydride (55% mineral oil suspension) in 200 ml of dimethoxyethane at 0° C., stirred for 1.5 hours, a solution of the aldehyde produced above is added in 50 ml of dimethoxyethane and stirred for 2 hours at 0° C. It is then mixed with saturated ammonium chloride solution, extracted with ether, washed with water, dried with magnesium sulfate and concentrated under vacuum. After chromatography of the residue on silica gel with hexane/ether (4+1). 17 g of α,β-unsaturated esters are obtained.

For hydrogenation, the ester is agitated at 25° C. in 750 ml of acetic acid with 1.6 g of palladium (10% carbon) for 6 hours under a hydrogen atmosphere. It is filtered and concentrated under vacuum. The residue is purified by bulb tube distillation at 0.2 Torr and 140° C. Thus, 11 g of the compound of the title is obtained as a colorless liquid.

IR: 2950, 2913, 2858, 1735, 1460, 1373, 1250, 1100, 831/m.

EXAMPLE 2

(5%)-(16RS)-2-decarboxy-5-fluoro-2-hydroxymethyl-6-methyl-18,18,19,19-tetradehydro-6a-carba-prostaglandin-I$_2$ 200 mg of (5%)-(16RS)-2-decarboxy-5-fluoro-2-hydroxymethyl-16-methyl-18,18,19,19-tetradehydro-6a-carba-prostaglandin-I$_2$-bis-(tetrahydropyranyl ether) (example 1) are stirred with 20 ml of a mixture of acetic acid/water/tetrahydrofuran (65+35+10) for 16 hours at 25° C. It is evaporated with addition of toluene and the residue is chromatographed on silica gel. With methylene chloride/ispropanol, 115 mg of the compound of the title are obtained as a colorless oil.

IR: 3600, 3410 (broad), 2925, 2870, 1602, 970/cm.

EXAMPLE 3

(5E)-(16RS)-5-fluoro-16-methyl-18,18,19,19-tetradehydro-6a-carba-prostaglandin-I$_2$ Analogously to example 1, 195 mg of the compound of the title are obtained as a colorless oil from 340 mg of the (5E)-(16RS)-2-decarboxy-5-fluoro-2-hydroxymethyl-16-methyl-18,18,19,19-tetradehydro-6a-carba-prostaglandin-I$_2$-11,15-bis-(tetrahydropyranyl ether) produced according to example 1.

IR: 3600, 3410 (broad), 2922, 1720, 1601, 970/cm.

EXAMPLE 4

(5%)-(16RS)-16,20-dimethyl-5-fluoro-18,18,19,19-tetradehydro-6a-carba-prostaglandin-I$_2$ Analogously to example 1, 290 mg of (5%)-(16RS)-2-decarboxy-16,20-dimethyl-5-fluoro-2-hydroxymethyl-18,18,19,19-tetradehydro-6a-carba-prostaglandin-I$_2$-11,15-bis-(tetrahydropyranyl ether) are obtained from 840 mg of (5E,Z)-(16RS)-2-decarboxy-5-fluoro-16,20-dimethyl-2-(dimethyl-tert-butylsilyloxymethyl)-18,18,19,19-tetradehydro-6a-carba-prostaglandin-I$_2$-11,15-bis-(tetrahydropyranyl ether and tetrabutylammonium fluoride. After oxidation and splitting off of the protective groups, 170 mg of the compound of the title are obtained as a colorless oil.

IR: 3600, 3410 (broad), 2921, 2868, 1719, 1601, 970/cm.

The starting material for the compound of the above title is produced as follows:

4a)(5E,Z)-(16RS)-2-decarboxy-5-fluoro-16,20-dimethyl-2-(dimethyl-tert-butylsilyloxymethyl)-18,18,19,19-tetradehydro-6a-carba-prostaglandin-I$_2$-11,15-bis-(tetrahydropyranyl ether)

Analogously to example 1a, 0.7 g of the compound of the title is obtained as a colorless oil from 1.8 g of (1R,5S,6R,7R)-7-(tetrahydropyran-2-yloxy)-6-[(E)-(3S,4RS)-4-methyl-3-(tetrahydropyran-2-yloxy)-non-1-ene-6-inyl]-bicyclo[3.3.0]-octan-3-one.

IR: 2947, 2870, 1451, 970, 835/cm.

EXAMPLE 5

(5%)-(16RS)-2-decarboxy-16,20-dimethyl-5-fluoro-2-hydroxymethyl-18,18,19,19-tetradehydro-6a-carba-prostaglandin-I$_2$ Analogously to example 2, 95 mg of the compound of the title are obtained as a colorless oil from 180 mg of (5%)-(16RS)-2-decarboxy-16,20-dimethyl-5-fluoro-2-hydroxymethyl-18,18,19,19-tetradehydro-6a-carba-prostaglandin-I$_2$-11,15-bis-(tetrahydropyranyl ether).

IR: 3600, 3400 (broad), 2925, 2868, 1601, 9071/cm.

EXAMPLE 6

(5Z)-5-fluoro-20-methyl-18,18,19,19-tetrahydro-16,16-trimethylene-6a-carba-prostaglandin-I$_2$ Analogously to the example, 320 mg of (5Z)-2-decarboxy-5-fluoro-2-hydromethyl-20-methyl-18,18,19,19-tetradehydro-16,16-trimethylene-6a-carba-prostaglandin-I$_2$-11,15-bis-(tetrahydropyranyl ether) are obtained from 920 mg of (5E,Z)-2-decarboxy-2-(dimethyl-tert-butylsilyloxymethyl)-5-fluoro-20-methyl-18,18,19,19-tetrahydro-16,16-trimethylene-6a-carba-prostaglandin-I$_2$-11,15-bis-(tetrahydropyranyl ether) and tetrabutylammonium fluoride. After oxidation and splitting off of the protective groups, 220 mg of the compound of the title are obtained as a colorless oil.

IR: 3610, 3400 (broad), 2920, 2870, 1720, 1601, 971/cm.

The starting material for the compound of the above title is produced as follows:

6a)

(5E,Z)-2-decarboxy-2-(dimethyl-tert-butylsilyloxymethyl)-5-fluoro-20-methyl-18,18,19,19-tetradehydro-16,16-trimethylene-6a-carba-prostaglandin-I$_2$-11,15-bis-(tetrahydropyranyl ether)

Analogously to example 1, 0.55 g of the compound of the title is obtained as a colorless oil from 1.4 g of (1R,5S,6R,7R)-7-(tetrahydropyran-2-yloxy)-6-[(E)-(3R)-3-tetrahydropyran-2-yloxy)-4,4-trimethylene-non-1-ene-6-inyl]-bicyclo[3.3.0]octan-3-one.

IR: 2950, 2868, 1451, 971, 835/cm.

EXAMPLE 7

5(Z)-2-decarboxy-5-fluoro-2-hydroxymethyl-20-methyl-18,18,19,19-tetradehydro-16,16-trimethylene-6a-carba-prostaglandin-I$_2$ Analogously to example 2, 70 mg of the compound of the title are obtained as a colorless oil from 120 mg (5Z)-2-decarboxy-5-fluoro-2-hydroxymethyl-20-methyl-18,18,19,19-tetradehydro-16,16-trimethylene-6a-carba-prostaglandin-I$_2$-11,15-bis-(tetrahydropyranyl ether).

IR: 3600, 3410 (broad), 2925, 2870, 1601, 970/cm.

EXAMPLE 8

(5Z)-16,16-dimethyl-5-fluoro-18,18,19,19-tetradehydro-6a-carba-prostaglandin-I$_2$ Analogously to example, 1, 310 mg of (5Z)-2-decarboxy-16,16-dimethyl-5-fluoro-2-hydroxymethyl-18,18,19,19-tetradehydro-6a-carba-prostaglandin-I$_2$-11,15-bis-(tetrahydropyranyl ether) are obtained from 0.9 g of (5E,Z)-2-decarboxy-16,16-dimethyl-2-(dimethyl-tert-butylsilyloxymethyl)-5-fluoro-18,18,19,19-tetradehydro-6a-carba-prostaglandin-I$_2$-11,15-bis-(tetrahydropyranyl ether) and tetrabutylammonium fluoride. After oxidation and splitting off of the protecting groups, 195 mg of the compound of the title are obtained as a colorless oil.

IR: 3600, 3420 (broad), 2922, 2868, 1718, 1600, 972/cm.

The starting material for the compound of the above title is produced as follows:

8a)

(5E,Z)-2-decarboxy-16,16-dimethyl-2-(dimethyl-tert-butylsilyloxymethyl)-5-fluoro-18,18,19,19-tetradehydro-6a-carba-prostaglandin-I$_2$-11,15-bis-(tetrahydropyranyl ether)

Analogously to example 1, 0.7 g of the compound of the title is obtained as a colorless oil from 1.6 g of (1R,5S,6R,7R)-7-tetrahydropyran-2-yloxy)-6-[(E)-(3R)-4,4-dimethyl-3-(tetrahydropyran-2-yloxy)-oct-1-ene-6-inyl]-bicyclo[3.3.0]octan-3-one.

IR: 2950, 2870, 1450, 972, 835/cm.

EXAMPLE 9

(5Z)-2-decarboxy-16,16-dimethyl-5-fluoro-2-hydroxymethyl-18,18,19,19-tetradehydro-6a-carba-prostaglandin-I$_2$ Analogously to example 2, 95 mg of the compound of the title are obtained as a colorless oil from 160 mg of (5Z)-decarboxy-16,16-dimethyl-5-fluoro-2-hydroxymethyl-18,18,19,19-tetradehydro-6a-carba-prostaglandin-I$_2$-11,15-bis-(tetrahydropyranyl ether).

IR: 3610, 3400 (broad), 2926, 2868, 1600, 972/cm.

EXAMPLE 10

(5Z)-5-fluoro-18,18,19,19-tetradehydro-16,16,20-trimethyl-6a-carba-prostaglandin-I$_2$ Analogously to example 1, 380 mg of (5Z)-2-decarboxy-5-fluoro-2-hydroxymethyl-18,18,19,19-tetradehydro-16,16,20-trimethyl-6a-carba-prostaglandin-I$_2$-11,15-bis-(tetrahydropyranyl ether) are obtained from 1.1 g of (5E,Z)-2-decarboxy-2-(dimethyl-tert-butylsilyloxymethyl)-5-fluoro-18,18,19,19-tetradehydro-16,16,20-trimethyl-6a-carba-prostaglandin-I$_2$-11,15-bis-(tetrahydropyranyl ether) and tetrabutylammonium fluoride. After oxidation and splitting off the protecting groups, 240 mg of the compound of the title are obtained as a colorless oil.

IR: 3610, 3400 (broad), 2925, 2870, 1718, 1602, 972/cm.

The starting material for the compound of the above title is produced as follows:

10a)

(5E,Z)-2-decarboxy-2-(dimethyl-tert-butylsilyloxymethyl)-5-fluoro-18,18,19,19-tetradehydro-16,16,20-trimethyl-6a-carba-prostaglandin-I$_2$-11,15-bis-(tetrahydropyranyl ether)

Analogously to example 1, 0.95 g of the compound of the title is obtained as a colorless oil from 1.8 g of (1R,5S,6R,7R)-7-(tetrahydropyran-2-yloxy)-6-[(E)-(3R)-4,4-dimethyl-3-(tetrahydropyran-2-yl)-non-1-en-6-inyl]-bicyclo[3.3.0]-octan-3-one.

IR: 2952, 2868, 1450, 972, 835/cm.

EXAMPLE 11

(5Z)-2-decarboxy-5-fluoro-2-hydroxymethyl-18,18,19,19-tetradehydro-16,16,20-trimethyl-6a-carba-prostaglandin-$I_2$ Analogously to example 2, 63 mg of the compound of the title are obtained as a colorless oil from 95 mg of (5Z)-2-decarboxy-5-fluoro-2-hydroxymethyl-18,18,19,19-tetradehydro-16,16,20-trimethyl-6a-carba-prostaglandin-$I_2$-11,15-bis-(tetrahydropyranyl ether).

IR: 3600, 3410 (broad), 2925, 2870, 1602, 970/cm.

EXAMPLE 12

(5Z)-(16RS)-16,19-dimethyl-18,19-didehydro-5-fluoro-6a-carba-prostaglandin-$I_2$ Analogously to example 1, 0.81 g of (5Z)-(16RS)-2-docarboxy-18,19-didehydro-16,19-dimethyl-5-fluoro-2-hydroxymethyl-6a-carba-prostaglandin-$I_2$-11,15-bis-(tetrahydropyranyl ether) is obtained from 2.1 g of (5E,Z)-(16RS)-2-decarboxy-18,19-didehydro-16,19-dimethyl-2-(dimethyl-tert-butylsilyloxymethyl)-5-fluoro-6a-carba-prostaglandin-$I_2$-1,15-bis-(tetrahydropyranyl ether) and tetrabutylammonium fluoride. After oxidation and splitting off of the protective groups 420 mg of the compound of the title are obtained as a colorless oil.

IR: 3600, 3420 (broad), 2925, 2870, 1720, 1601, 974/cm.

The starting material for the compound of the above title is produced as follows:

12a)

(5E,Z)-(16RS)-2-decarboxy-18,19-didehydro-16,19-dimethyl-2-(dimethyl-tert-butylsilyloxymethyl)-5-fluoro-6a-carba-prostaglandin-$I_2$-11,15-bis-(tetrahydropyranyl ether)

Analogously to example 1, 0.84 g of the compound of the title is obtained as a colorless oil from 1.7 g of (1R,5S,6R,7R)-7-(tetrahydropyran-2-yloxy)-6-[(E)-(3R,4RS)-4,7-dimethyl-3-(tetrahydropyran-2-yloxy)-octa-1,6-dienyl]-bicyclo[3.3.0]octan-3-one.

IR: 2955, 2870, 1450, 974, 835/cm.

EXAMPLE 13

(5Z)(16RS)-2-decarboxy-18,19-didehydro-16,19-dimethyl-5-fluoro-2-hydroxymethyl-6a-carba-prostaglandin-$I_2$ Analogously to example 2, 90 mg of the compound of the title are obtained as a colorless oil from (5Z)-(16RS)-2-decarboxy-18,19-didehydro-16,19-dimethyl-5-fluoro-2-hydroxymethyl-6a-carba-prostaglandin-$I_2$-11,15-bis-(tetrahydropyranyl ether).

IR: 3600, 3400 (broad), 2925, 2870, 1602, 974/cm.

EXAMPLE 14

(5Z)-(16RS)-13,14-didehydro-5-fluoro-16-methyl-18,18,19,19-tetradehydro-6a-carba-prostaglandin-$I_2$ Analogously to example 1, 0.79 g of (5Z)-(16RS)-2-decarboxy-13,14-didehydro-5-fluoro-2-hydroxymethyl-16-methyl-18,18,19,19-tetradehydro-6a-carba-prostaglandin-$I_2$-11,15-bis-(tetrahydropyranyl ether) are obtained from 2 g of (5E,Z)-(16RS)-decarboxy-13,14-didehydro-2-(dimethyl-tert-butylsilyloxymethyl)-5-fluoro-16-methyl-18,18,19,19-tetradehydro-6a-carba-prostaglandin-$I_2$-11,15-bis-(tetrahydropyranyl ether) and tetrabutylammonium fluoride. After oxidation and splitting off of the protective groups, 400 mg of the compound of the title are obtained as colorless oil.

IR: 3600, 3405 (broad), 2928, 2872, 2221, 1720, 1600/cm.

The starting material for the compound of the above title is produced as follows:

14a)

(5E,Z)-(16RS)-2-decarboxy-13,14-didehydro-2-(dimethyl-tert-butylsilyloxymethyl)-5-fluoro-16-methyl-18,18,19,19-tetradehydro-6a-carba-prostaglandin-$I_2$-11,15-bis-(tetrahydropyranyl ether)

Analogously to example 1, 1.05 g of the compound of the title are obtained as a colorless oil from 2.0 g of (1R,5S,6S,7R)-7-(tetrahydropyran-2-yloxy)-6-[(E)-(3S,4RS)-4-methyl-3-(tetrahydropyran-2-yloxy)-octa-1,6-diinyl)-bicyclo-[3.3.0]octan-3-one.

IR: 2956, 2875, 2221, 1458/cm.

EXAMPLE 15

(5Z)-2-decarboxy-13,14-didehydro-5-fluoro-2-hydroxymethyl-16-methyl-18,18,19,19-tetradehydro-6a-carba-prostaglandin-$I_2$ Analogously to example 2, 55 mg of the compound of the title are obtained as a colorless oil from (5Z)-(16RS)-2-descarboxy-13,14-didehydro-5-fluoro-2-hydroxymethyl-16-methyl-18,18,19,19-tetradehydro-6a-carba-prostaglandin-$I_2$-11,15-bis-(tetrahydropyranyl ether).

IR: 3600, 3402 (broad), 2930, 2873, 2223, 1105, 1020/cm.

EXAMPLE 16

(5Z)-(16RS)-13,14-didehydro-16,20-dimethyl-5-fluoro-18,18,19,19-tetradehydro-6a-carba-prostaglandin-$I_2$ Analogously to example 1, 0.71 g of (5Z)-(16RS)-2-decarboxy-13,14-didehydro-16,20-dimethyl-5-fluoro-2-hydroxymethyl-18,18,19,19-tetradehydro-6a-carba-prostaglandin-$I_2$-11,15-bis-tetrahydropyranyl ether) are obtained from 1.90 g of (5E,Z)-(16RS)-2-decarboxy-13,14-didehydro-16,20-dimethyl-2-(dimethyl-tert-butylsilyloxymethyl)-5-fluoro-18,18,19,19-tetradehydro-6a-carba-prostaglandin-$I_2$-11,15-bis-(tetrahydropyranyl ether) and tetrabutylammonium fluoride. After oxidation and splitting off of the protective groups, 320 mg of the compound of the title are obtained as a colorless oil.

IR: 3600, 3405 (broad), 2926, 2870, 2221, 1715, 1110, 1025/cm.

16a)

(5E,Z)-(16RS)-2-decarboxy-13,14-didehydro-16,20-dimethyl-2-(dimethyl-tert-butylsilyloxymethyl)-5-fluoro-18,18,19,19-tetradehydro-6a-carba-prostaglandin-$I_2$-11,15-bis-(tetrahydropyranyl ether)

Analogously to example 1, 1.39 g of the compound of the title are obtained as a colorless oil from 2.80 g of (1R,5S,6S,7R)-7-(tetrahydropyran-2-yloxy)-6-[(3S,4RS)-4-methyl-3-(tetrahydropyran-2-yloxy)-nona-1,6-diinyl]-bicyclo[3.3.0]octan-3-one IR: 2951, 2872, 2220, 1460/cm.

EXAMPLE 17

(5Z)-(16RS)-2-decarboxy-13,14-didehydro-16,20-dimethyl-5-fluoro-2-hydroxy-methyl-18,18,19,19-tetradehydro-6a-carba-prostaglandin-$I_2$ Analogously to example 2, 70 mg of the compound of the title are obtained as a colorless oil from (5Z)-(16RS)-2-decarboxy-13,14-didehydro-16,20-dimethyl-5-fluoro-2-hydroxymethyl-18,18,19,19-tetradehydro-6a-carba-prostaglandin-$I_2$-11,15-bis-(tetrahydropyranyl ether)

IR: 3600, 3400 (broad), 2938, 2875, 2219, 1108, 1021/cm.

EXAMPLE 18

(5Z)-13,14-didehydro-5-fluoro-20-methyl-18,18,19,19-tetradehydro-16,16-trimethylene-6a-carba-prostaglandin-$I_2$ Analogously to example 1, 0.75 g of (5Z)-2-decarboxy-13,14-didehydro-5-fluoro-2-hydroxymethyl-20-methyl-18,18,19,19-tetradehydro-16,16-trimethylen-6a-carba-prostaglandin-$I_2$-11,15-bis-(tetrahydropyranyl ether) is obtained from 2.0 g of (5E,Z)-2-decarboxy-13,14-didehydro-2-(dimethyl-tert-butylsilyloxymethyl)-5-fluoro-20-methyl-18,18,19,19-tetradehydro-16,16-trimethylene-6a-carba-prostaglandin-$I_2$-11,15-bis-(tetradehydropyranyl ether) and tetrabutylammonium fluoride. After oxidation and splitting off of the protective groups, 328 mg of the compound of the title are obtained as a colorless oil.

IR: 3600, 3420 (broad), 2930, 2871, 2220, 1718, 1115, 1020/cm.

18a)
(5E,Z)-2-decarboxy-13,14-didehydro-2-(dimethyl-tert-butylsilyloxymethyl)-5-fluoro-20-methyl-18,18,19,19-tetradehydro-16,16-trimethylene-6a-carba-prostaglandin-$I_2$-11,15-bis-(tetrahydropyranyl ether)

Analogously to example 1, 1.21 g of the compound of the title are obtained as a colorless oil from 2.5 g of (1R,5S,6S,7R)-7-(tetrahydropyran-2-yloxy)-6-[(3S)-3-(tetrahydropyran-2-yloxy)-4,4-trimethylene-nonal,6-diinyl]-bicyclo[3.3.0]octan-3-one IR: 2952, 2868, 2218, 1458/cm.

EXAMPLE 19

(5Z)-2-decarboxy-13,14-didehydro-5-fluoro-2-hydroxymethyl-20-methyl-18,18,19,19-tetradehydro-16,16-trimethylene-6a-carba-prostaglandin-$I_2$ Analogously to example 2, 52 mg of the compound of the title are obtained as a colorless oil from 100 mg of (5Z)-2-decarboxy-13,14-didehydro-5-fluoro-2-hydroxymethyl-20-methyl-18,18,19,19-tetradehydro-16,16-trimethylene-6a-carba-prostaglandin-$I_2$-11,15-bis-(tetrahydropyranyl ether).

IR: 3600, 3410 (broad), 2932, 2868, 2223, 1130, 1020/cm.

EXAMPLE 20

(5Z)-13,14-didehydro-5-fluoro-18,18,19,19-tetradehydro-16,16,20-trimethyl-6a-carba-prostaglandin-$I_2$ Analogously to example 1, 0.71 g of (5Z)-2-decarboxy-13,14-didehydro-5-fluoro-2-hydroxymethyl-18,18,19,19-tetradehydro-16,16,20-trimethyl-6a-carba-prostaglandin-$I_2$-11,15-bis-(tetrahydropyranyl ether) is obtained from 2 g of (5E,Z)-2-decarboxy-13,14-didehydro-2-(dimethyl-tert-butylsilyloxymethyl)-5-fluoro-18,18,19,19-tetradehydro-16,16,20-trimethyl-6a-carba-prostaglandin-$I_2$-bis-(tetrahydropyranyl ether) and tetrabutylammonium fluoride. After oxidation and splitting off of the protective groups, 380 mg of the compound of the title are obtained as a colorless oil.

IR: 3600, 3410 (broad), 2938, 2870, 2225, 1713, 1120, 1018/cm.

20a)
(5E,Z)-2-decarboxy-13,14-didehydro-2-(dimethyl-tert-butylsilyloxymethyl)-5-fluoro-18,18,19,19-tetradehydro-16,16,20-trimethyl-6a-carba-prostaglandin-$I_2$-11,15-bis-(tetrahydropyranyl ether)

Analogously to example 1, 2.45 g of the compound of the title are obtained as a colorless oil from 4.5 g of (1R,5S,6S,7R)-7-(tetrahydropyran-2-yloxy)-6-[(3S)-4,4-dimethyl-3-(tetrahydropyran-2-yloxy)-nona-1,6-diinyl]-bicyclo[3.3.0]octan-3-one.

IR: 2951, 2873, 2220, 1451/cm.

EXAMPLE 21

(5Z)-2-decarboxy-13,14-didehydro-5-fluoro-2-hydroxymethyl-18,18,19,19-tetradehydro-16,16,20-trimethyl-6a-carba-prostaglandin-$I_2$ Analogously to example 2, 82 mg of the compound of the title are obtained as a colorless oil from 150 mg of (5Z)-2-decarboxy-13,14-didehydro-5-fluoro-2-hydroxymethyl-18,18,19,19-tetradehydro-16,16,20-trimethyl-6a-carba-prostaglandin-$I_2$-11,15-bis-(tetrahydropyranyl ether)

IR: 3600, 3405 (broad), 2935, 2870, 2220, 1128, 1021/cm.

EXAMPLE 22

(5Z)-(16RS)-5-fluoro-16-methyl-18,18,19,19-tetrahydro-6a-carba-prostaglandin-$I_2$-methyl ester An ether solution of diazomethane is dripped into a solution of 150 mg of (5Z)-(16RS)-5-fluoro-16-methyl-18,18,19,19-tetradehydro-6a-carba-prostaglandin-$I_2$ in 10 ml of dichloromethane at 0° C. until permanent yellow coloration. After another 5minutes. It is concentrated and under vacuum and the residue is purified by chromatography on silica gel. 130 mg of the compound of the title are eluted as a colorless oil with toluene/2Z isopropyl alcohol.

IR: 3600, 2937, 2866, 1450, 1435, 1025, 976cm.

EXAMPLE 23

(5Z)-(16RS)-5-fluoro-16-methyl-18,18,19,19-tetrahydro-6a-carba-prostaglandin-$I_2$-acetylamide 63 mg of triethylamine are added at 20° C. to a solution of 260 mg of (5Z)-(16RS)-5-fluoro-16-methyl-18,18,19,19-tetradehydro-6a-carba-prostaglandin-$I_2$-11,15-bis-(tetrahydropyranyl ether) in 8 ml of acetonitrile, cooled to 0° C., and a solution of 47 mg of acetylisocyanate in 5 ml of acetonitrile is dripped in. It is concentrated under vacuum at 2 hours at 20° diluted with 100 ml of citrate buffer (pH5), extracted with ether, the extract is successively washed with sodium bicarbonate solution and brine, dried on magnesium sulfate and evaporated under vacuum. For splitting off of the protective groups, the residue is stirred in 10 ml of glacial acetic acid/water tetrahydrofuran (65/35/10) overnight at 20° C. and evaporated under vacuum to dryness. The residue is chromatographed on silica gel with dichloromethane/1 isopropyl alcohol. 98 mg of the compound of the title are obtained as a colorless oil.
IR: 3600, 3410, 2952, 2835, 1710, 976/cm.

EXAMPLE 24

(5Z)-(16RS)-5-fluoro-16-methyl-18,18,19,19-tetradehydro-6a-carba-prostaglandin-$I_2$-carboxamide.

A solution of 200 mg of (5Z)-(16RS)-5-fluoro-16-methyl-18,18,19,19-tetradehydro-6a-carba-prostaglandin-$I_2$ in 6 ml dimethylformamide is mixed at 0° C. with 65 mg of triethylamine and 90 mg of chloroformic acid isobutyl ester. After 30 minutes, dry ammonia gas is introduced into the solution for 15 minutes. It is allowed to stand for 2 hours at 20° C. diluted with citrate buffer (pH5), extracted several times with ethyl acetate, the extract is washed with sodium bicarbonate solution and brine, dried on magnesium sulfate and evaporated under vacuum. After chromatography of the residue on silica gel with dichloromethane 1–5% isopropanol, 152 mg of the compound of the title are obtained as a colorless oil.
IR: 3600, 3500, 3410, 2952, 2871, 1666, 974/cm.

EXAMPLE 25

(5Z)-(16RS)-5-fluoro-16-methyl-18,18,19,19-tetradehydro-6a-carba-prostaglandin-$I_2$-(2,3-dihydroxy-propyl)-amide 240 mg of (5Z)-(16RS)-5-fluoro-16-methyl-18,18,19,19-tetradehydro-6a-carba-prostaglandin-$I_2$ are dissolved in 5 ml of acetone and mixed at 0° C. with 74 mg of triethylamine and 100 mg of chloroformic acid butyl ester. After 20 minutes, a solution of 300 mg of 1-amino-2,3-dihydroxypropane in 6 ml of acetone and 6 ml of acetonitrile is added, stirred for 2 hours at 20° C. concentrated under vacuum, diluted with 100 ml of dichloromethane, agitated with 5 ml of brine, dried on magnesium sulfate and evaporated under volume. After chromatography of the residue on silica gel, 195 mg of the compound of the title are obtained with methylene chloride/20% isopropyl alcohol.
IR: 3600, 3410 (broad), 2935, 2865, 1648, 1030, 976/cm.

EXAMPLE 26

(5Z)-(16RS)-5-fluoro-16-methyl-18,18,19,19-tetrahydro-6a-carba-prostaglandin-$I_2$-phenacyl ester 240 mg of (5Z)-(16RS)-5-fluoro-16-methyl-18,18,19,19-tetradehydro-6a-carba-prostaglandin-$I_2$ are dissolved in 10 ml of acetone, mixed with 150 mg of ω-bromoacetophenone and 2 ml of triethylamine and stirred overnight at room temperature. It is mixed with 200 ml of ether, agitated successively with water and brine, dried on magnesium sulfate and evaporated under vacuum. The residue is purified by chromatography on silica gel with methylene chloride 5% acetone and 235 mg of the compound of the title are obtained.
IR: 3600, 2935, 2862, 1740, 1702, 1601, 976/cm.

EXAMPLE 27

(5Z)-(16RS)-2-decarboxy-5-fluoro-16-methyl-2-(2-oxazolin-2-yl)-18,18,19,19-tetradehydro-6a-carba-prostaglandin-$I_2$ 189 mg of (5Z)-(16RS)-5-fluoro-16-methyl-18,18,19,19-tetradehydro-6a-carba-prostaglandin-$I_2$ are suspended in 5 ml of hexamethyldisilazane and heated to 140° C. for 1.5 h under argon. Excess reagent is removed under vacuum.

The residue is dissolved in 5 ml of absolute acetonitrile, 786 ml of triphenylphonphine and 1.05 ml of triethylamine are added and with ice cooling 0.5 ml of a 1 M solution of ethanolamine in acetonitrile is dripped in. Then, 1.5 ml of a 1 M solution of carbon tetrachloride in acetonitrile is added and allowed to stand overnight at 20° C. After concentration under vacuum, it is washed five times with 75 ml hexane each time. The crystals that are formed are separated from the oily residue and the oil residue is dissolved in 15 ml of methanol and mixed at 0° with 5 ml of 2 N sodium hydroxide solution and stirred for 30 minutes at 20° C. After concentration under vacuum to about 5 ml, it is mixed with 10 ml of water and extracted four times with 10 ml of ethyl acetate each time. After drying on magnesium sulfate and evaporation, 250 mg of oil residue are obtained, which is chromatographed on silica gel with dichloromethane/5% isopropyl alcohol. 120 mg of the compound of the title are obtained as an oil.

EXAMPLE 28

(5Z)-(16RS)-5-fluoro-16-methyl-18,18,19,19-tetradehydro-6a-carba-prostaglandin-$I_2$-tris-(hydroxymethyl)-aminomethane salt A solution of 60 mg of tris-(hydroxymethyl)-aminoethane in 0.2 ml of water is added to a solution of 179 mg of (5Z)-(16RS)-5-fluoro-16-methyl-18,18,19,19-tetradehydro-6a-carba-prostaglandin-$I_2$ in 35 ml of acetonitrile at 70° C. It is allowed to cool with stirring, decanted from the solvent after 16 hours and the residue is dried under vacuum. 154 mg of the compound of the title are isolated as a waxy mass.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 5-fluorocarbacyclin of the formula

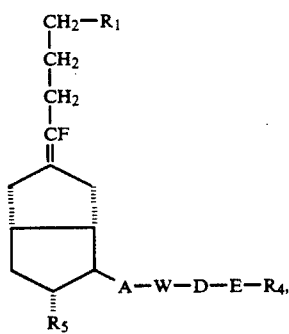

wherein
$R_1$ is —$CH_2OH$ or

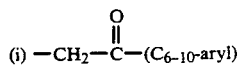

wherein $R_2$ is (a) hydrogen, (b) $C_{1-10}$ alkyl, (c) $C_{1-10}$ alkyl substituted by halogen; hydroxy; $C_{1-4}$ alkoxy; $C_{6-10}$ aryl; $C_{6-10}$ aryl substituted by 1–3 halogen atoms, a phenyl group, 1–3 $C_{1-4}$-alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$-alkylammonium; (d) $C_{5-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group, (h) an aromatic heterocycle of 5 or 6 ring atoms one of which is O, N or S, the remainder being carbon atoms, or

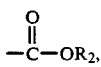

wherein the aryl group is unsubstituted or substituted by (a) 1–3 phenyl groups, each of which is unsubstituted or substituted by 1–3 halogen atoms; (B) 1–3 $C_{1-4}$-alkoxy groups; or (C) 1–3 halogen atoms;

$R_1$ is

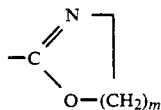

wherein m is 1 or 2,
or $R_1$ is

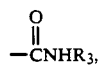

wherein $R_3$ is $R_2$ or the acyl group of a $C_{1-10}$-hydrocarbon carboxylic or sulfonic acid;

W is —CHOR—, or

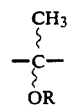

wherein the OR-group is in the α- or β-position;
R is tetrahydropyranyl, tetrahydrofuanyl, α-ethoxyethyl, trimethylsilyl, dimethyl-tert-butylsilyl, tribenzylsilyl or an acyl group of a $C_{1-10}$-hydrocarbon carboxylic or sulfonic acid;

A is —CH$_2$—CH$_2$—, trans—CH═CH—, or —C≡C—,

D is

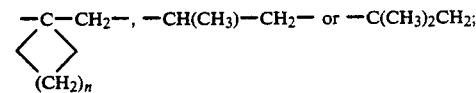

n is 1, 2 or 3;
E is —C≡C— in the 18, 19-position (prostacyclin nomenclature),
$R_5$ is OR;
$R_4$ is (a) a $C_{1-10}$ hydrocarbon aliphatic radical, (b) a $C_{1-10}$ hydrocarbon aliphatic radical substituted by $C_{6-10}$ aryl or by $C_{6-10}$ aryl substituted by 1–3 halogen atoms; a phenyl group, 1–3 $C_{1-4}$ alkyl groups or a chloromethyl, fluoromethyl, trifluoromethyl, carboxy, hydroxy or $C_{1-4}$ alkoxy group; (c) $C_{3-10}$ cycloalkyl, (d) $C_{3-10}$ cycloalkyl substituted by $C_{1-4}$ alkyl, (e) $C_{6-10}$ aryl, (f) $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy groups, (g) an aromatic heterocycle of 5 or 6 ring atoms one of which is O, N and S, the remainder being carbon atoms;

or when $R_2$ is H, a physiologically compatible salt thereof with a base.

2. (5Z)-(16RS)-5-fluoro-16-methyl-18,18,19,19-tetradehydro-6a-carba-prostaglandin-I$_2$, a compound of claim 1.

3. (5Z)-(16RS)-2-decarboxy-5-fluoro-2-hydroxymethyl-16-methyl-18,18,19,19-tetradehydro-6a-carba-prostaglandin-I$_2$, a compound of claim 1.

4. (5E)-(16RS)-5-fluoro-16-methyl-18,18,19,19-tetradehydro-6a-carba-prostaglandin-I$_2$, a compound of claim 1.

5. (5Z)-(16RS)-16,20-dimethyl-5-fluoro-18,18,19,19-tetradehydro-6a-carba-prostaglandin-I$_2$, a compound of claim 1.

6. (5Z)-(16RS)-2-decarboxy-16,20-dimethyl-5-fluoro-2-hydroxymethyl-18,18,19,19-tetradehydro-6a-carba-prostaglandin-I$_2$, a compound of claim 1.

7. (5Z)-5-fluoro-20-methyl-18,18,19,19-tetradehydro-16,16-trimethylene-6a-carba-prostaglandin-I$_2$, a compound of claim 1.

8. (5Z)-2-decarboxy-5-fluoro-2-hydroxymethyl-20-methyl-18,18,19,19-tetradehydro-16,16-trimethylene-6a-carba-prostaglandin-I$_2$, a compound of claim 1.

9. (5Z)-16,16-dimethyl-5-fluoro-18,18,19,19-tetradehydro-6a-carba-prostaglandin-I$_2$, a compound of claim 1.

10. (5Z)-2-decarboxy-16,16-dimethyl-5-fluoro-2-hydroxymethyl-18,18,19,19-tetradehydro-6a-carba-prostaglandin-I$_2$, a compound of claim 1.

11. (5Z)-5-fluoro-18,18,19,19-tetradehydro-16,16,20-trimethyl-6a-carba-prostaglandin-I$_2$, a compound of claim 1.

12. (5Z)-2-decarboxy-5-fluoro-2-hydroxymethyl-18,18,19,19-tetradehydro-16,16,20-trimethyl-6a-carba-prostaglandin-I$_2$, a compound of claim 1.

13. (5Z)-(16RS)-13,14-didehydro-5-fluoro-16-methyl-18,18,19,19-tetradehydro-6a-carba-prostaglandin-I$_2$, a compound of claim 1.

14. (5Z)-(16RS)-2-decarboxy-13,14-didehydro-5-fluoro-2-hydroxymethyl-16-methyl-18,18,19,19-tetradehydro-6a-carba-prostaglandin-I$_2$, a compound of claim 1.

15. (5Z)-(16RS)-13,14-didehydro-16,20-dimethyl-5-fluoro-18,18,19,19-tetradehydro-6a-carba-prostaglandin-I$_2$, a compound of claim 1.

16. (5Z)-(16RS)-2-decarboxy-13,14-didehydro-16,20-dimethyl-5-fluoro-2-hydroxymethyl-18,18,19,19-tetradehydro-6a-carba-prostaglandin-I$_2$, a compound of claim 1.

17. (5Z)-13,14-didehydro-5-fluoro-20-methyl-18,18,19,19-tetradehydro-16,16-trimethylene-6a-carba-prostaglandin-I$_2$, a compound of claim 1.

18. (5Z)-2-decarboxy-13,14-didehydro-5-fluoro-2-hydroxymethyl-20-methyl-18,18,19,19-tetradehydro- 16,16-trimethylene-6a-carba-prostaglandin-I$_2$, a compound of claim 1.

19. (5Z)-13,14-didehydro-5-fluoro-18,18,19,19-tetradehydro-16,16,20-trimethyl-6a-carba-prostaglandin-I$_2$, a compound of claim 1.

20. (5Z)-2-decarboxy-13,14-didehydro-5-fluoro-2-hydroxymethyl-18,18,19,19-tetradehydro-16,16,20-trimethyl-6a-carba-prostaglandin-I$_2$, a compound of claim 1.

21. (5Z)-(16RS)-5-fluoro-16-methyl-18,18,19,19-tetradehydro-6a-carba-prostaglandin-I$_2$-methyl ester, a compound of claim 1.

22. (5Z)-(16RS)-5-fluoro-16-methyl-18,18,19,19-tetradehydro-6a-carba-prostaglandin-I$_2$-acetylamide, a compound of claim 1.

23. (5Z)-(16RS)-5-fluoro-16-methyl-18,18,19,19-tetradehydro-6a-carba-prostaglandin-I$_2$-carboxamide, a compound of claim 1.

24. (5Z)-(16RS)-5-fluoro-16-methyl-18,18,19,19-tetradehydro-6a-carba-prostaglandin-I$_2$-(2,3-dihydroxypropyl)-amide, a compound of claim 1.

25. (5Z)-(16RS)-5-fluoro-16-methyl-18,18,19,19-tetradehydro-6a-carba-prostaglandin-I$_2$-phenacyl ester, a compound of claim 1.

26. (5Z)-(16RS)-2-decarboxy-5-fluoro-16-methyl-2-(2-oxazolin-2-yl)-18,18,19,19-tetrahydro-6a-carba-prostaglandin-I$_2$, a compound of claim 1.

27. (5Z)-(16RS)-5-fluoro-16-methyl-18,18,19,19-tetradehydro-6a-carba-prostaglandin-I$_2$-tris-(hydroxymethyl)-aminomethane-salt, a compound of claim 1.

28. A pharmaceutical composition comprising an amount of a compound of claim 1 effective to inhibit thrombocyte aggregation and a pharmaceutically acceptable carrier.

29. A compound of claim 1 wherein —A—W—D—E—R$_4$ is

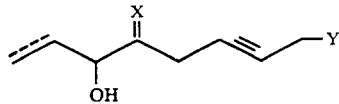

wherein $=\!=\!=\!=$
represents a double or triple bond;
Y is H or CH$_3$; and
$=$X is H, CH$_3$; CH$_3$, CH$_3$; or

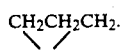

30. A method of inhibiting the aggregation of thrombocytes in a patient in need of such treatment comprising administering an effective amount of a compound of claim 1.

31. A method of achieving a bronchodilatory effect comprising administering a compound of claim 1.

32. A compound of claim 1, wherein R$_1$ is CH$_2$OH.

33. A compound of claim 1, wherein R$_1$ is COOR$_2$.

34. A method of claim 30, wherein R$_1$ is COOR$_2$.

* * * * *